United States Patent [19]

Cherkofsky

[11] 4,438,117
[45] Mar. 20, 1984

[54] 2-SUBSTITUTEDTHIO-4,5-DIARYLPYRIMI-DINES

[75] Inventor: Saul C. Cherkofsky, Wilmington, Del.

[73] Assignee: E. I. Du Pont de Nemours and Company, Wilmington, Del.

[21] Appl. No.: 183,336

[22] Filed: Sep. 3, 1980

[51] Int. Cl.$^3$ .................. A61K 31/505; C07D 239/22
[52] U.S. Cl. ...................................... 424/251; 544/315; 544/316; 544/318
[58] Field of Search ................ 424/251; 544/315, 316, 544/318

[56] References Cited

U.S. PATENT DOCUMENTS

| 3,251,850 | 5/1966 | Kühle et al. | 544/318 |
| 3,772,272 | 11/1973 | Hardtmann et al. | 544/315 |
| 3,836,529 | 9/1974 | Santilli et al. | 544/316 |
| 3,892,860 | 7/1975 | Hardtmann et al. | 424/251 |
| 3,959,471 | 5/1976 | Hardtmann et al. | 424/251 |
| 4,159,338 | 6/1979 | Cherkofsky et al. | 548/336 |
| 4,182,769 | 1/1980 | Cherkofsky et al. | 548/336 |
| 4,190,666 | 2/1980 | Cherkofsky et al. | 548/336 |
| 4,267,184 | 5/1981 | Cherkofsky et al. | 548/517 |

FOREIGN PATENT DOCUMENTS 343176  1/1960  Switzerland .................. 544/318

OTHER PUBLICATIONS

Srivastava, et al., "Chemical Abstracts," vol. 85, 1976, col. 201764f.
Baddar, et al., "Chemical Abstracts," vol. 85, 1976, col. 32950f.
Baddar, et al., "J. Het. Chem.", vol. 15, 1978, pp. 105–112.
Coppola, et al., "J. H. Chem.", vol. 16, 1979, pp. 545–554.
Mantegazza, et al., "Arch. Intern. Pharmacodynami", vol. 95, 1952, pp. 123–152.
Ruggieri, et al., "Gazzetta", vol. 92, 1962, pp. 768–798.
Claison, et al., "Ber.", vol. 22, 1889, pp. 3373–3381.
Siegmund, et al., "Proc. Soc. Exp. Biol. Med.", vol. 95, 1957, pp. 721–731.
Thompson, "Bact. Rev.", vol. 11, 1947, pp. 115–145.
Gibson, "Remington's Pharm. Sciences," 16th Ed., 1980, pp. 3–4.
Raynolds, et al., "J.A.C.S.", vol. 82, 1960, pp. 472–474.
Abramovitch, *Pyridines and Its Derivatives*, vol. 14, 1975, pp.

*Primary Examiner*—Donald G. Daus
*Assistant Examiner*—James H. Turnipseed

[57] ABSTRACT

2-Substitutedthio-4,5-diarylpyrimidines, such as 2-(1,1,2,2-tetrafluoroethylthio)-4,5-bis(4-methoxyphenyl)pyrimidine useful for treating arthritis and/or alleviating pain.

18 Claims, No Drawings

2-SUBSTITUTED THIO-4,5-DIARYLPYRIMIDINES

BACKGROUND OF THE INVENTION

This invention relates to diarylpyrimidines which possess antiinflammatory and/or analgesic properties.

U.S. Pat. Nos. 3,959,471; 3,892,860 and 3,772,272 disclose 1-alkyl-4,6-diarylpyrimidine-2(1H)-ones and their use as tranquilizers, sleep inducers and antiinflammatory agents. F. G. Baddar, et al., J. Het. Chem., 15, 105 (1978) disclose 2-methylthio-4,6-diarylpyrimidines.

G. M. Coppola, J. Het. Chem., 16, 545 (1979) discloses 4,5-diaryl-2(1H)-pyrimidinones and 1-alkyl-4,5-diarylpyrimidinones and the antiinflammatory activity of the latter class of compounds. P. Mantegazza, et al., Arch.Intern. Pharmacodynamie, 95, 123 (1952) discloses 2-mercapto-4,5-diphenylpyrimidine and its central nervous system activity.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

Also, there is a continuing need for safe and effective analgesic agents.

The compounds of the present invention possess antiinflammatory and/or analgesic properties.

SUMMARY OF THE INVENTION

This invention relates to novel compounds which possess antiinflammatory and/or analgesic properties, pharmaceutical compositions containing them, and methods of use of these compunds to treat arthritis and/or alleviate pain in mammals.

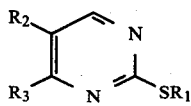

wherein $R_1$=mono or polyfluoro $C_1$-$C_2$ alkyl or $C_1$-$C_2$ alkyl;
$R_2$ and $R_3$ independently=3-pyridyl or

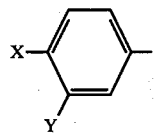

where
X=H, F, Cl, OCH$_3$, OCH$_2$CH$_3$, S(O)$_n$CH$_3$, or di($C_1$-$C_2$alkyl)amino;
n=0, 1 or 2;
Y=H or Cl provided when Y=Cl, X must=Cl; provided $R_2$ and $R_3$ cannot both be phenyl; provided also that when

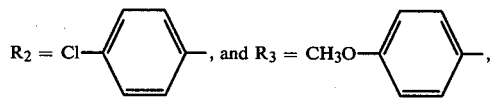

then $R_1$ cannot=$CF_2CHF_2$; and pharmaceutically suitable salts thereof.

Preferred compounds for utility considerations and/or ease of synthesis are where $R_1$=mono or polyfluoro $C_1$-$C_2$ alkyl; or $R_2$ and $R_3$ independently=

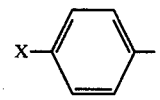

where
X=F, Cl, OCH$_3$ or S(O)$_n$CH$_3$; and
n=0, 1 or 2.

Examples of specifically preferred compounds are
2-(1,1,2,2-tetrafluoroethylthio)-4,5-bis(4-methoxyphenyl)pyrimidine; and
2-methylthio-4-(4-methoxyphenyl)-5-(4-chlorophenyl)-pyrimidine.

Synthesis

Compounds of the invention where $R_1$=$CF_3$ may be prepared by the reaction of a 2-mercapto-4,5-diarylpyrimidine in liquid ammonia, optionally in the presence of a cosolvent such as tetrahydrofuran, with trifluoromethyl iodide in the presence of an ultraviolet light source.

Compounds of the invention where $R_1 \neq CF_3$ may be prepared by the reaction of a 2-mercapto-4,5-diarylpyrimidine with an alkylating agent. Within the context of the invention, tetrafluoroethylene and other fluorinated olefins are considered alkylating agents as are dimethyl sulfate and alkyl halides and sulfonates. The reaction is carried out in a solvent such as acetone, methanol, ethanol or dimethylformamide in the presence of a base such as potassium carbonate or diisopropylamine at a temperature from $-20°$ to the boiling point of the solvent. Those skilled in the art will recognize that when the alkylating agent is a gas at atmospheric pressure in the temperature range specified, it may be desirable to conduct the alkylation reaction in a pressure vessel.

2-Mercapto-4,5-diarylpyrimidines may be prepared by the reaction of thiourea with a 1,2-diarylpropane-1,3-dione. Reactions of α-formyl ketones with thiourea to give 2-mercapto pyrimidines are known in the art, see for example Gazzetta, 92, 768 (1962).

The preparation of formyl desoxybenzoin from desoxybenzoin is described in Ber, 22, 3278 (1889). Those skilled in the art will recognize that other 1,2-diarylpropane-1,3-diones may be prepared by appropriate modification of this procedure.

The compounds of this invention and their synthesis are illustrated further by the following examples. All temperatures are in degrees Centigrade.

EXAMPLE 1

2-(1,1,2,2-Tetrafluoroethylthio)-4,5-bis(4-methoxyphenyl)pyrimidine (a) α-Formyl desoxyanisoin A solution of sodium methoxide (11.9 g, 0.22 mole) in 80 ml ethanol was cooled in an ice bath and treated with ethyl formate (20 ml, 0.24 mole). A solution of desoxyanisoin (51.2 g, 0.2 mole) in 275 ml warm tetrahydrofuran was then added while maintaining the reaction temperature below 5°. The reaction mixture was stirred for 1 hour at 0° and then stirred overnight at room temperature.

A small amount of precipitate was removed by filtration and the filtrate concentrated to ~100 ml on the rotary evaporator. It was then diluted with ~1 l water and the solution filtered to recover 29.5 g of starting material. The filtrate was cooled in an ice bath and acidified with 1 N sulfuric acid. The resultant solid was collected, washed with water and dried to give the title compound (24.25 g), m.p. 129°–132°. Infrared and H-NMR spectra were consistent with the assigned structure.

(b) 2-Mercapto-4,5-bis(4-methoxyphenyl)-pyrimidine

A solution of α-formyl desoxyanisoin (21.3 g, 75 mmole) and thiourea (9.75 g, 1.7 equiv) in 375 ml ethanol was treated with 3 N HCl (7.5 ml) and heated at reflux for 3.5 hours. The reaction mixture was concentrated on the rotary evaporator and the residue recrystallized from ethanol to give the title compound (11.6 g), m.p. 188°–191°. Infrared and H-NMR spectra were consistent with the assigned structure.

(c) 2-(1,2,2-Tetrafluoroethylthio)-4,5-bis(4-methoxyphenyl)pyrimidine

2-Mercapto-4,5-bis(4-methoxyphenyl)pyrimidine (5.4 g), diisopropylamine (4.2 ml) and dimethylformamide (150 ml) were charged into a stainless steel bomb. The bomb was cooled and evacuated, charged with tetrafluoroethylene (2.25 g) and agitated for 12 hours at 60°. The reaction mixture was poured into 700 ml ice water and then extracted with ethyl acetate. The organic extract was washed with water and brine, dried and concentrated. Chromatography on silica gel and recrystallization from ethanol gave the title compound (4.4 g) m.p. 118°–120°. Infrared and H-NMR spectra were consistent with the assigned structure. MS 424 (M+), 323 (M-CF$_2$CF$_2$H).

Anal. Calcd for C$_{20}$H$_{16}$N$_2$O$_2$SF$_4$: C,. 56.59; H, 3.80 N, 6.60 Found: C, 57.3; H, 3.96; N, 6.88.

EXAMPLE 2

2-Trifluoromethylthio-4,5-bis(4-fluorophenyl)-pyrimidine

2-Mercapto-4,5-bis(4-fluorophenyl)pyrimidine (5.04 g) was placed in a flask into which was condensed ~125 ml liquid ammonia. The resultant slurry was diluted with 30 ml tetrahydrofuran and cooled to −78°. Trifluoromethyl iodide (1.9 ml) was introduced as a gas and the cold bath was then removed. The reaction mixture was irradiated with a General Electric 275 W sun lamp for 2 hours. The ammonia was allowed to evaporate and the tetrahydrofuran removed in vacuo. The residue was dissolved in methylene chloride, washed with water and brine, dried and concentrated on the rotary evaporator. Crystallization from ethanol gave the title compound (2.1 g), m.p. 80°–83°. Infrared and H-NMR were consistent with the assigned structure. MS 368 (M+).

Anal. Calcd. for C$_{17}$H$_9$N$_2$SF$_5$: C, 55.43; H, 2.46, N, 7.61. Found: C, 55.6; H, 2.60; N, 7.62.

EXAMPLE 3

2-Methylthio-4-(4-methoxyphenyl)-5-(4-chlorophenyl)-pyrimidine

A mixture of 2-mercapto-4-(4-methoxyphenyl)-5-(4-chlorophenyl)pyrimidine* (7 g) and potassium carbonate (8 g) in 200 ml acetone was treated with methyl iodide (4.8 ml) and stirred 5 hours at room temperature. The reaction mixture was filtered and concentrated on the rotary evaporator. Chromatography on silica gel and crystallization from ethanol gave the title compound (3.4 g), m.p. 127°–130°. Infrared and H-NMR spectra were consistent with the assigned structure. MS 342 (M+).

*Containing ~20 mole percent 4-chlorobenzyl 4-methoxyphenyl ketone

Anal. Calcd. for C$_{18}$H$_{15}$N$_2$OClS: C, 63.05; H, 4.41; N, 8.17. Found: C, 63.0; H, 4.35; N, 7.99.

The following compounds can be prepared following the procedures outlined above and illustrated in the preceding examples.

TABLE 1

$$\begin{array}{c} R_2 \\ R_3 \end{array} \diagup\hspace{-1em}\diagdown \begin{array}{c} N \\ N \end{array} SR_1$$

| Example No. | R$_1$ | R$_2$ | R$_3$ | melting point °C. |
|---|---|---|---|---|
| 1 | CF$_2$CF$_2$H | 4-CH$_3$OC$_6$H$_4$ | 4-CH$_3$OC$_6$H$_4$ | 118–120 |
| 2 | CF$_3$ | 4-FC$_6$H$_4$ | 4-FC$_6$H$_4$ | 80–83 |
| 3 | CH$_3$ | 4-ClC$_6$H$_4$ | 4-CH$_3$OC$_6$H$_4$ | 127–130 |
| 4 | CF$_2$CF$_2$H | 4-FC$_6$H$_4$ | 4-FC$_6$H$_4$ | 65–88 |
| 5 | CF$_2$CF$_2$H | 4-FC$_6$H$_4$ | 4-CH$_3$SC$_6$H$_4$ | |
| 6 | CF$_3$ | 4-CH$_3$OC$_6$H$_4$ | 4-CH$_3$OC$_6$H$_4$ | 105–108 |
| 7 | CF$_3$ | 4-ClC$_6$H$_4$ | 4-CH$_3$OC$_6$H$_4$ | 100–101 |
| 8 | CF$_3$ | 4-FC$_6$H$_4$ | 4-CH$_3$SO$_2$C$_6$H$_4$ | |
| 9 | CH$_3$ | 4-CH$_3$OC$_6$H$_4$ | 4-CH$_3$OC$_6$H$_4$ | 95–98 |
| 10 | C$_2$H$_5$ | 4-FC$_6$H$_4$ | 4-FC$_6$H$_4$ | |
| 11 | CH$_2$CF$_3$ | 4-CH$_3$OC$_6$H$_4$ | 4-CH$_3$OC$_6$H$_4$ | |
| 12 | CF$_2$CF$_2$H | 4-FC$_6$H$_4$ | 3-pyridyl | |
| 13 | CF$_2$CF$_2$H | 4-FC$_6$H$_4$ | 4-C$_2$H$_5$OC$_6$H$_4$ | |
| 14 | CH$_3$ | C$_6$H$_5$ | 3,4-diClC$_6$H$_3$ | |
| 15 | CF$_3$ | 4-FC$_6$H$_4$ | 4-(CH$_3$)$_2$NC$_6$H$_4$ | |

Dosage Forms the anti-arthritic agents and/or analgesic agents of this invention can be administered to treat arthritis and/or alleviate pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 1 to 100 milligrams per kilogram of body weight. Ordinarily 2 to 50, and preferably 5 to 25 milligrams per kilogram per day given in divided doses 2 to 4 times a day or in sustained release form is effective to obtain desired results.

Dosage forms (compositions) suitable for internal administration contain from about 25 milligrams to about 900 milligrams of active ingredient per unit. In these pharmaceutical compositions the active ingredient will ordinarily be present in an amount of about 5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in Remington's Pharmaceutical Sciences, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Pharmaceutical Utility

A procedure for detecting and comparing the antiinflammatory activity of compounds in this series and standard drugs for which there is a good correlation with human efficacy is the adjuvant-induced arthritis test in rats.

A procedure for detecting and comparing the analgesic activity of compounds in this series and standard drugs for which there is a good correlation with human efficacy is the phenylquinone writhing test.

The test procedures employed for determining antiinflammatory and analgesic activity are described below.

Established Adjuvant-Induced Arthritis in Rats

Charles River Lewis male rats (130–150 grams) are injected subcutaneously in plantar area of the right hind paw with 0.1 ml of adjuvant (Difco heat-killed, lyophilized Mycobacterium butyricum suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum Acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control Mean Paw Volume (ml)} - \text{Treatment Group Mean Paw Volume (ml)}}{\text{Arthritic Control Mean Paw Volume (ml)} - \text{Non-Arthritic Control Mean Paw Volume (ml)}} \times 100 =$$

% Decrease from Control Mean Paw Volume.

Dose-response regression lines of the % decrease are plotted on semi-log paper by visual fit and the ED50% decrease from control paw volume is determined by inspection. Alternatively, % reduction in paw volume was measured at a dose of 27 mg/kg.

Phenylquinone Writhing Test

The phenylquinone writhing test, modified from Siegmund, et al., Proc. Soc. Exp. Biol. Med. 95, 729 (1957), was employed. A test compound suspended in 1% methylcellulose was given orally to fasted (17–21 hours) female white mice, 5–20 animals per double blind test. Aqueous (0.01% phenyl-p-benzoquinone) phenylquinone was injected intraperitoneally 24 minutes later using 0.20 ml per mouse. Commencing 30 minutes after the oral administration of the test compound, the mice were observed for 10 minutes for a characteristic stretching or writhing syndrome which is indicative of pain induced by phenylquinone. The effective analgesic dose for 50% of the mice (ED$_{50}$) was calculated by the moving average method of Thompson, W. R., Bact. Rev., 11, 115–145 (1947).

TABLE 2

| | Biological Data | | |
|---|---|---|---|
| Example No. | AA ED$_{50}$ Mg/kg | % Reduction @ 27 mg/kg | PQW ED$_{50}$ mg/kg |
| 1 | 25 | — | >108 |
| 2 | — | 37* | >108 |
| 3 | — | 39* | >108 |
| 4 | — | 0 | 45 |
| 6 | — | 32* | 48 |
| 7 | — | 0 | 49 |
| 9 | — | 16** | 108 |

*p <0.05 compared to control by student's "t"test.
**p >0.1 compared to control.

What is claimed is:

1. A compound of the formula

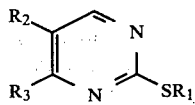

wherein

R$_1$=mono or polyfluoro C$_1$–C$_2$ alkyl or C$_1$–C$_2$ alkyl;

R$_2$ and R$_3$ independently=3-pyridyl or

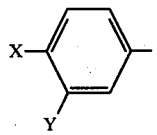

where X=H, F, Cl, OCH$_3$, OCH$_2$CH$_3$, S(O)$_n$CH$_3$, or di(C$_1$–C$_2$ alkyl)amino;

n=0, 1 or 2;

Y=H or Cl provided when Y=Cl,

X must=Cl;

provided R$_2$ and R$_3$ cannot both be phenyl; provided also that when

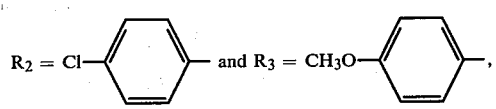

then R$_1$ cannot=CF$_2$CHF$_2$; or a pharmaceutical suitable salt thereof.

2. A compound of claim 1 wherein
R$_1$=mono or polyfluoro C$_1$–C$_2$ alkyl.

3. A compound of claim 1 wherein

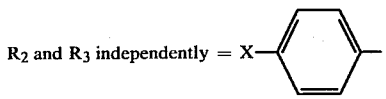

where X=F, Cl, OCH$_3$ or S(O)$_n$CH$_3$;
n=0, 1 or 2.

4. A compound of claim 1 wherein
R$_1$=mono or polyfluoro C$_1$–C$_2$ alkyl;

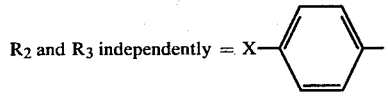

where X=F, Cl, OCH$_3$ or S(O)$_n$CH$_3$;
n=0, 1 or 2.

5. The compound of claim 1 which is 2-(1,1,2,2-tetrafluoroethylthio)-4,5-bis(4-methoxyphenyl)pyrimidine.

6. The compound of claim 1 which is 2-methylthio-4-(4-methoxyphenyl)-5-(4-chlorophenyl)pyrimidine.

7. A pharmaceutical composition consisting essentially of an effective antiinflammatory or analgesic amount of a compound of claim 1.

8. A pharmaceutical composition consisting essentially of an effective antiinflammatory or analgesic amount of a compound of claim 2.

9. A pharmaceutical composition consisting essentially of an effective antiinflammatory or analgesic amount of a compound of claim 3.

10. A pharmaceutical composition consisting essentially of an effective antiinflammatory or analgesic amount of a compound of claim 4.

11. A pharmaceutical composition consisting essentially of an effective antiinflammatory amount of the compound of claim 5.

12. A pharmaceutical composition consisting essentially of an effective antiinflammatory amount of the compound of claim 6.

13. A method for treating arthritis or alleviating pain in a mammal which comprises administering to the mammal an effective antiarthritic or analgesic amount of a compound of claim 1.

14. A method for treating arthritis or alleviating pain in a mammal which comprises administering to the mammal an effective antiarthritic or analgesic amount of a compound of claim 2.

15. A method for treating arthritis or alleviating pain in a mammal which comprises administering to the mammal an effective antiarthritic or analgesic amount of a compund of claim 3.

16. A method for treating arthritis or alleviating pain in a mammal which comprises administering to the mammal an effective antiarthritic or analgesic amount of a compound of claim 4.

17. A method for treating arthritis in a mammal which comprises administering to the mammal an effective antiarthritic amount of the compound of claim 5.

18. A method for treating arthritis in a mammal which comprises administering to the mammal an effective antiarthritic amount of the compound of claim 6.

* * * * *